(12) United States Patent
Bousquet et al.

(10) Patent No.: US 7,153,969 B2
(45) Date of Patent: Dec. 26, 2006

(54) HYDROXYACETIC ESTER DERIVATIVES, PREPARATION METHOD AND USE AS SYNTHESIS INTERMEDIATES

(75) Inventors: André Bousquet, Sisteron (FR); Andrée Musolino, Volonne (FR)

(73) Assignee: Sanofi-Aventis, Paris (FR)

( * ) Notice: Subject to any disclaimer, the term of this patent is extended or adjusted under 35 U.S.C. 154(b) by 122 days.

(21) Appl. No.: 10/890,749

(22) Filed: Jul. 14, 2004

(65) Prior Publication Data

US 2004/0260110 A1 Dec. 23, 2004

Related U.S. Application Data

(62) Division of application No. 10/425,437, filed on Apr. 29, 2003, now Pat. No. 6,894,186, which is a division of application No. 09/509,879, filed as application No. PCT/FR98/02082 on Sep. 29, 1998, now Pat. No. 6,573,381.

(30) Foreign Application Priority Data

Oct. 6, 1997 (FR) .................................. 97 12441

(51) Int. Cl.
*C07D 471/02* (2006.01)

(52) U.S. Cl. ........................ 546/114; 546/112; 546/113; 549/50; 549/59; 560/60; 560/1; 560/8; 560/55

(58) Field of Classification Search ................ 546/114, 546/112, 113; 549/59, 50; 560/60, 1, 8, 560/55

See application file for complete search history.

(56) References Cited

U.S. PATENT DOCUMENTS

| 4,529,596 A | 7/1985 | Aubert et al. |
| 5,036,156 A | 7/1991 | Bouisset et al. |
| 5,132,435 A | 7/1992 | Bousquet et al. |
| 5,189,170 A | 2/1993 | Bouisset et al. |
| 5,204,469 A | 4/1993 | Descamps et al. |

FOREIGN PATENT DOCUMENTS

| EP | 099 802 | 2/1984 |
| EP | 420 706 | 4/1991 |
| EP | 465 358 | 1/1992 |
| EP | 466 569 | 1/1992 |

*Primary Examiner*—Thurman K. Page
*Assistant Examiner*—Chukwuma Nwaonicha
(74) *Attorney, Agent, or Firm*—Paul E. Dupont; James W. Bolcsak

(57) ABSTRACT

Methyl (R)-2-($R_1OSO_2$)-2-(2-chlorophenyl)acetates useful as intermediates in the preparation of methyl (S)-2(2-chlorophenyl)-2-(4,5,6,7-tetrahydrothieno[3,2-c]-5-pyridyl)acetate.

11 Claims, No Drawings

HYDROXYACETIC ESTER DERIVATIVES, PREPARATION METHOD AND USE AS SYNTHESIS INTERMEDIATES

CROSS REFERENCE TO RELATED APPLICATIONS

This application is a divisional of U.S. application Ser. No. 10/425,437 filed Apr. 29, 2003, now U.S. Pat. No. 6,894,186 which in turn is a divisional of U.S. application Ser. No. 09/509,879 filed Oct. 6, 2000, now U.S. Pat. No. 6,573,381, which in turn is a 35 U.S.C. § 371 application of PCT International Application No. PCT/FR98/02082 filed Sep. 29, 1998.

The present invention concerns, in a general fashion, new derivatives of hydroxyacetic esters, and their use as synthesis intermediates.

More specially, the object of the invention is the sulphonyloxyacetic esters with the general formula:

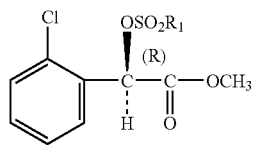

in which $R_1$ represents a benzyl group, a $C_1$–$C_4$ alkyl, which may be substituted by one or several halogen atoms, such as chlorine or bromine, or a phenyl group, which may be substituted by one or several halogen atoms or by one or several linear or branched $C_1$–$C_4$ alkyl groups or by a nitro group.

In particular, the invention concerns formula-I compounds in which $R_1$ represents a methyl, ethyl, propyl, trifluoromethyl, benzyl, phenyl, chlorophenyl, tolyl, trimethylphenyl, triisopropylphenyl, dichlorophenyl in particular 2,5-dichlorophenyl or nitrophenyl, in particular p-nitrophenyl, group.

Formula-I compounds have demonstrated themselves to be particularly useful as intermediates, notably for the synthesis of methyl (S)-2(2-chlorophenyl)-2(4,5,6,7-tetrahydrothieno[3,2-c]-5-pyridyl)acetate or clopidrogel.

This enantiomer, which has the following structural formula:

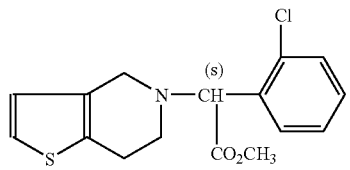

is known for its therapeutic value, notably for its inhibition of platelet aggregation and antithrombotic properties.

In patent EP 0465358, a process is described for the preparation of the (R) and (S) enantiomers of 2-(halogenophenyl)-2-(4,5,6,7-tetrahydrothieno[3,2-c]-5-pyridyl)acetate of a $C_1$–$C_4$ alkyl, using 2-arylacetic esters with a labile group in the 2 position.

According to this process:

a) racemic a $C_1$–$C_4$ alkyl 2-(halogenophenyl)-2-halogeno or a $C_1$–$C_4$ alkylsulphonyloxy, or $C_6$–$C_{10}$ alkyl arylsulphonyloxy)acetate is coupled with 4,5,6,7-tetrahydrothieno[3,2-c]pyridine in the form of a base or salt to obtain a racemic compound.

b) the racemate thus formed is resolved by recrystallising optically active acid salts to obtain the desired (R) or (S) enantiomers.

However, the only example given of this process started from racemic methyl 2(2-chlorophenyl)-2-chloroacetate for the final preparation of clopidogrel and no precise indication or example was given to illustrate the preparation of a $C_1$–$C_4$ alkyl 2-(halophenyl)-2-(bromo or alkylsulfonyloxy or arylsulphonyloxy)-acetate According to this example, clopidogrel is obtained by carrying out the following 5 steps, starting from a 2-hydroxyacetic ester:

a) and b) reaction of racemic 2(2-chlorophenyl)-2-hydroxyacetic acid with phosphorus pentachloride and esterification with methanol to form racemic methyl 2-(2-chlorophenyl)-2-chloroacetate with a 45% yield, c) coupling of the methyl 2-(2-chlorophenyl)-2-chloroacetate formed in this way, with 4,5,6,7-tetrahydrothieno[3,2-c]pyridine in the presence of potassium carbonate, which yields racemic methyl 2-(4,5,6,7-tetrahydrothieno[3,2-c]-5-pyridyl)-2(2-chlorophenyl)-acetate, with a mean yield of 80%, d) resolution of the racemate obtained by salification with camphosulphonic acid (yield: 88% in terms of the salt desired)

e) regeneration of clopidogrel in basic form by treating the camphosulphonic salt in question with sodium bicarbonate Using this process, clopidogrel is obtained with a chemical yield of up to 30% from 2(2-chlorophenyl)-2-hydroxyacetic acid.

During the preliminary trials carried out in the context of the present invention, an attempt was made to prepare clopidogrel or its (R) enantiomer by means of an analogous reaction to that described in the patent already referred to, but starting from the (R) or (S) enantiomer of methyl 2(2-chlorophenyl)-2-chloroacetate.

However, all the tests performed in methanol, acetonitrile or ethyl acetate as solvent at a temperature between room temperature and 65° C., with 1 or 2 equivalents of 4,5,6,7-tetrahydrothieno[3,2-c]pyridine either in the form of the base or in the form of the hydrochloride, with or without sodium bicarbonate, led to the production of 72 to 88% of racemic methyl 2(2-chlorophenyl)-2(4,5,6,7-tetrahydrothieno[3,2-c]-5-pyridyl)acetate Other tests carried out with heating to 80° C. and using methyl (S)-2(2-chlorophenyl)-2-chloroacetate and 4,5,6,7-tetrahydrothieno[3,2-c]pyridine in the presence of sodium carbonate and in a solvent mixture of methylisobutyl ketone/water yielded methyl (R)-2(4,5,6,7-tetrahydrothieno[3,2-c]-5-pyridyl)-2(chlorophenyl)acetate with an entantiomeric excess of only 20%.

Consequently, the development of a process for the preparation of clopidogrel from 4,5,6,7-tetrahydrothieno[3,2-c]pyridine using a stereoselective method, which involves as few steps as possible and providing an appreciable yield of the desired compound remains of incontestable importance.

It has been discovered rather surprisingly, according to the invention, that clopidogrel can be obtained in just 3 steps from (R)-2(2-chlorophenyl)-2-hydroxyacetic acid with a global yield of the order of 80% by replacing the methyl-(R)-2(2-chlorophenyl)-2-halogenoacetate, by methyl-(R)-2(2-chlorophenyl)-acetate, which has a sulphonyloxy group in the 2 position, i.e. a compound with the above formula I.

This process is all the more surprising because:

A) the 2-methanesulphonyloxy groups and 2-toluenesulphonyloxy groups of carboxyl esters are known to undergo racemisation when they are involved in a nucleophilic substitution by an amine function (Angew. Chem. Int. Ed. Eng. 22 (1983), no. 1 pp 65–66).

These claims have been confirmed in *Tetrahedron*, Vol. 47, no. 7, pp 1109–1135 (1991), where it is reported that the 2-methanesulphonyloxy and 2-p-toluenesulphonyloxy esters of carboxylic acids are inappropriate substrates for a stereoselective nucleophilic substitution reaction in the 2 position.

Similar observations have been published in Leibigs. Ann. Chem. 1986, p. 314–433, where yields of <30% are reported as being obtained during the substitution of methyl-2-p-toluenesulphonyloxy- or methyl-2-methanesulphonyloxy-propionate with benzylamine.

B) The (R) and (S) enantiomers of 2-sulphonyloxyacetic esters, which include an additional 2-phenyl group, are known to produce compounds with considerably reduced stereoselectivity after nucleophilic substitution in the 2-position.

For example, *Tetrahedron*, Vol. 44, no. 17, pp 5583–5595 (1988) reports the substitution of derivatives of (S) or (R) methyl-2-triflyloxy-2-X-acetate by O-benzylhydroxylamine in dichloromethane as a solvent and at a temperature between 0° C. and room temperature in order to form the (R) and (S) acetic esters of 2-O-benzylhydroxylamino-2-X respectively. As is known, the triflyl group designates the trifluoromethylsulphonyl radical.

This reaction is found to be highly selective in the case of esters in which X represents an alkyl group, which may be substituted, such as methyl or benzyl (enantiomeric excess, ee≧95%), but has much lower selectivity when X represents the phenyl group since the enantiomeric excess of the corresponding (R)-2-O-benzylhydroxylamino-2-phenyl ester is no more than 50%. Very similar results have been reported after other experiments carried out using 2-sulphonyloxy derivatives of 2-phenylacetic esters.

Thus:

a) *Tetrahedron Letters*, Vol. 31, no. 21, pp 2953–2956 (1990) describes the substitution reaction of the methyl (S)-2-triflyloxy-2-X-acetate esters with t-butyloxycarbonyl-hydrazine or BOC-hydrazine, in dichloromethane and at 0° C., to form (R)-2-BOC-hydrazinyl-2-X-acetic esters.

The selectivity of this reaction has also been shown to be very considerable when X represents an alkyl group, which may be substituted, such as methyl, isobutyl or benzyl (ee≧95%), but in contrast, very limited when X represents phenyl (ee: 28%).

b) *Tetrahedron*, Vol. 48, no. 15, pp 3007–3020 (1992) reports the substitution of methyl (S)-2-nosyloxy-2-X-acetate derivatives with an azido group, the reaction taking place in dichloromethane and at room temperature, in order to form (R)-2-azido-2-X acetic esters.

Once more, the substitution of the 2-sulphonyloxy group, in this case the nosyloxy group, takes place in a highly selective manner when X represents an alkyl group, which may be substituted, such as methyl, isopropyl, sec-butyl or benzyl (ee>92%), but disappointing when X represents the phenyl group (ee: 35%).

These latter findings actually led the authors of the publication in question to conclude that "the phenyl group is well known for reducing stereoselectivity when the esters of 2-nosyloxy and 2-triflyloxy esters are substituted by different classes of nucleophilic agents". As is known, the nosyl group designates the p-nitrophenylsulphonyl radical.

The sulphonyloxy derivatives of formula-I acetic esters that have shown themselves to be particularly interesting synthesis intermediates, notably for the preparation of clopidogrel are:

methyl (R)-2-benzenesulphonyloxy-2(2-chlorophenyl)acetate methyl (R)-2(2-chlorophenyl)-2(p-toluenesulphonyloxy)acetate methyl (R)-2(2-chlorophenyl)-2-methanesulphonyloxy acetate methyl (R)-2(4-chlorobenzenesulphonyloxyl)-2-(2-chlorophenyl)acetate methyl (R)-2(2-chlorophenyl)-2(2,4,6-trimethylbenzenesulphonyloxy)acetate methyl (R)-2(2-chlorophenyl)-2(2,4,6-triisopropylbenzenesulphonyloxy)acetate methyl (R)-2(2-chlorophenyl)-2(4-nitrobenzenesulphonyloxy)acetate methyl (R)-2(2-chlorophenyl)-2(2,5-dichlorobenzenesulphonyloxy)acetate In particular, the following are preferred methyl (R)-2-benzenesulphonyloxy-2(2-chlorophenyl)acetate methyl (R)-2(2-chlorophenyl)-2(2,4,6-trimethylbenzenesulphonyloxy)acetate methyl (R)-2(2-chlorophenyl)-2(2,4,6-triisopropylbenzenesulphonyloxy)acetate methyl (R)-2(2-chlorophenyl)-2(4-nitrobenzenesulphonyloxy)acetate methyl (R)-2(4-chlorobenzenesulphonyloxyl)-2(2-chlorophenyl)acetate methyl (R)-2(2-chlorophenyl)-2(2,5-dichlorobenzenesulphonyloxy)acetate.

The sulphonyloxy derivatives of the invention can be obtained by reacting the (R)-2(2-chlorophenyl)-2-hydroxy acetic ester with the formula:

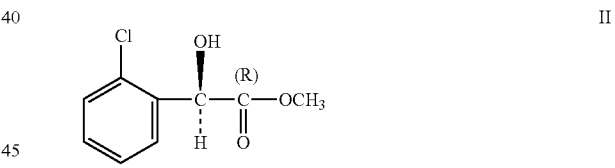

II with a sulphonyl anhydride or halogenide, with the general formula $R_1-SO_2-R_2$        III in which $R_2$ represents an $OSO_2-R_1$ group or, preferably, a halogen atom such as chlorine or bromine, and $R_1$ has the same significance as before, in the presence of a lithium salt and an aromatic amine which acts both as a catalyst and acid acceptor such as pyridine or 4-dimethylaminopyridine, which yields the desired compound.

The reaction in question is generally carried out in an aprotic solvent, such as a $C_1-C_4$ aliphatic hydrocarbide, preferably halogenated, for instance dichloromethane, dichloroethane, chloroform, carbon tetrachloride or tetrachloroethane, and at a temperature between 0° C. and room temperature.

In addition, the aromatic amine, preferably $C_6-C_{10}$, is used in stoechiometric quantity or preferably a slight excess which can reach 1.2 molar equivalent in terms of the formula-III compound.

The coupling reaction of the formula-II and formula-III compounds in which $R_2$ represents a halogen atom, can give rise to a side reaction which results in the formation of a halogenated derivative i.e. a methyl 2(2-chlorophenyl)-2-halogenoacetate derivative.

However, it was fortuitously noticed that the presence of a lithium salt in the reaction mixture makes it possible to reduce this side reaction considerably and consequently to obtain high proportions of the formula-I compound.

By way of example, the reaction between methyl (R)-2 (2-chlorophenyl)-2-hydroxyacetate with p-nitrobenzenesulphonyl chloride or p-toluenesulphonyl chloride in dichloromethane at 20° C. and in the presence of pyridine and lithium perchlorate, produces a yield of 92% of methyl (R)-2(2-chlorophenyl)-2-(p-nitrobenzenesulphonyloxy)acetate and a yield of 85% of methyl (R)(2-chlorophenyl)-2 (p-toluenesulphonyloxy)acetate respectively after 5 hours, whereas the same reaction, conducted in the absence of lithium perchlorate produces yields of only 28% and 30% of the end product respectively.

This lithium salt, which can be for example, lithium perchlorate ($LiClO_4$) or lithium tetrafluoroborate ($LiBF_4$), is used in a stoechiometric quantity. However, it is preferable to take a slight excess of this lithium salt, that is up to 1.2 molar equivalent in terms of the formula-III compound.

As for the formula-II ester, it can be obtained using a non-racemating reaction by esterifying (R)-2(2-chlorophenyl)-2-hydroxyacetic acid or (R)-2-chloro-mandelic acid, which is a commercial product, with methanol and in the presence of a strong acid, such as sulphuric acid.

According to a variant of the above process, formula-I sulphonyloxy derivatives can also be prepared by reacting the formula-II ester with a formula-III halogenide in the presence of 4-dimethylaminopyridine as catalyst and another acid acceptor, such as an aliphatic amine, for example triethylamine to produce the desired compound.

The reaction is generally conducted at a temperature of −10° C. to +10° C., preferably at 0° C., and in an aprotic solvent, such as one of those already mentioned, notably dichloromethane.

The processes described above make it possible to obtain formula-I sulphonyloxy derivatives with particularly good yields, usually of the order of 90 to 98% and with quite remarkable enantiomeric excesses of >99%.

As previously indicated, the sulphonyloxy derivatives of the invention can be used notably for the preparation of clopidogrel.

In consequence, another object of the invention concerns the preparation of clopidogrel by a process in which 4,5,6,7-tetrahydrothieno[3,2-c]pyridine in the form of a base or salt with a formula-I sulphonyloxy derivative in the presence of a basic agent used alone or in aqueous solution, which yields the desired compound.

The reaction medium used is usually a polar solvent, such as a $C_2$–$C_5$ aliphatic ester, for example ethyl or isopropyl acetate, a $C_1$–$C_4$ aliphatic alcohol, N,N-dimethylformamide, a $C_4$–$C_6$ cyclic ester or a $C_2$–$C_6$ aliphatic ester such as tetrahydrofuran or isopropyl ether, a $C_2$–$C_8$ aliphatic ketone, for example methylisobutylketone or, preferably, a non-polar solvent, such as a $C_1$–$C_4$ halogenated aliphatic hydrocarbon, for example dichloromethane, dichloroethane, chloroform, carbon tetrachloride or tetrachloroethane or a $C_6$–$C_{10}$ aromatic hydrocarbon, for example benzene, toluene or a xylene so that a two-phase system is formed if water is present in the reaction medium. In this latter case, if necessary, a phase-transfer catalyst can be used, such as a quaternary ammonium, a phosphonium salt or a crown ether.

Similarly, the basic agent can be a carbonate of an alkali metal, such as sodium or potassium carbonate, or a bicarbonate of an alkali metal, for instance sodium or potassium bicarbonate, and the reaction can be conducted at a temperature ranging from ambient temperature to the reflux temperature of the medium used.

As for the 4,5,6,7-tetrahydrothieno[3,2-c]pyridine, a known compound, it is used in a stoechiometric quantity but usually and preferably in an excess which can be as much as 2.5 molar equivalents in terms of the formula-I sulphonyloxy derivative.

By conducting this latter reaction in toluene, methylisobutylketone or isopropyl acetate at a temperature of 80° C. over about 4 hours, it is possible to obtain clopidogrel with a chemical yield in excess of 95% and with an enantiomeric excess of between 80 and 88%.

Using dichloromethane as the solvent and at a temperature of 40° C.:

a) the percentage converted into clopidogrel can reach 94 to 95% in 5 hours with an enantiomeric excess of 96%.

b) starting from methyl (R)-2-(4-chlorobenzenesulphonyloxy)-2(2-chlorophenyl)acetate, the conversion into clopidogrel reaches 100% after 10 hours and the enantiomeric excess is 96%.

c) starting from methyl (R)-2(2-chlorophenyl)-2(4-nitrobenzenesulphonyloxy)acetate, the conversion into clopidogrel reaches 100% after 30 minutes and the enantiomeric excess is >98%.

Using an alternative pathway, clopidogrel can also be prepared from sulphonyloxy derivatives of the invention and 2(thien-2-yl)ethylamine.

Consequently, the invention also applies to the preparation of clopidogrel according to a process in which:

a) 2(thien-2-yl)ethylamine in the form of the base or salt is reacted with a formula-I sulphonyloxy derivative in the presence in a basic agent used alone or in aqueous solution, to form methyl (+)-(S)-α(2(thien-2-yl)ethylamino)-α-(2-chlorophenyl)acetate, which has the formula:

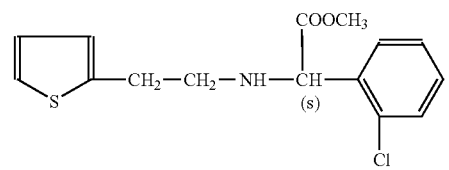

IV b) the thienylethylamine derivative thus formed is reacted with an formylation agent and cyclised in the presence of an acid, which yields the desired compound.

The formylation agent used in the above process can be:

either formic aldehyde or any compound generally known to release it in a reactive form, such as for example its hydrate or its polymerisation derivatives. These formylation agents can be considered to be preferred in the context of the invention.

or compounds with the general formula:

V in which $R_3$ represents a halogen atom, a $C_1$–$C_4$ alkyloxy group, a $C_1$–$C_4$ alkylthio group or an amino group and $R_4$ represents a $C_1$–$C_4$ alkoxy group, a $C_1$–$C_4$ alkylthio group, a $C_2$–$C_5$ alkoxycarbonyl or phenoxycarbonyl group or heterocyclic compounds with the general formula:

in which Z represents O, NH, or S, such as s-trioxane.

The step involving the use of 2(thien-2-yl)ethylamine, a known compound, can be conducted under the same operating conditions as those described previously for the use of 4,5,6,7-tetrahydrothieno[3,2-c]pyridine The formylation and cyclisation step can give rise to intermediate compounds, such as a hydroxymethyleneamine or a heterocycle of the trimethylenetriamine type, as reported in patent EP 0 466 569.

Consequently, the reactions with the formylation and cyclisation agent can be carried out successively, possibly by isolating the intermediate compounds in question, or conversely, they can take place simultaneously.

When the reactions occur successively, the step involving the formylation agent can be carried out optionally in the presence of an ether, a hydrocarbon solvent, such as benzene, toluene, xylene or petroleum ether or of a halogenated solvent, such as methylene chloride or dichloroethane.

The cyclisation is then carried out in a polar solvent, such as water, an alcohol, dimethylformamide or in a mixture of these solvents.

As the formylation agent, formic aldehyde is generally preferred and this can be added to the reaction medium in the form of an aqueous solution.

The acid can be an organic or inorganic acid, in general a strong acid, such as sulphuric acid, or a hydracid, such as hydrochloric acid, or a sulphonic acid, such as methanesulphonic acid.

When the reactions are carried out simultaneously, the reaction medium consists of a polar solvent, such as water or an alcohol, and the acid, which can be inorganic or organic, is added to the medium, preferably in stoechiometric quantity in terms of the formula-IV compound employed. In this case, this acid is a strong acid which can be simply added to the medium in the form of its salt with the formula-IV compound. An acidic solvent such as formic acid or acetic acid can also be used, the former combined with paraformaldehyde being particularly preferred.

Clopidogrel is obtained according to the invention, that is by using the various methods described above, can then be purified if necessary, by a conventional method using a recrystallisation process or by chromatographic procedures.

The following non-exhaustive examples illustrate the invention.

Preparation

Methyl (R)-2-hydroxy-2(2-chlorophenyl)acetate

A 1000-ml reactor fitted with a double jacket and a valve in the bottom, a mechanical stirrer, a thermometer and a condenser is loaded with 120 g (0.643 mole) of (R)-2-hydroxy-2(2-chlorophenyl)acetic acid, 480 ml of methanol and 4.8 g of 95% sulphuric acid. The solution obtained is then heated under reflux for 2 hours and the excess methanol is then eliminated under reduced pressure. The oily residue is then taken up in 650 ml of dichloromethane and 240 g of an aqueous solution of 10% potassium carbonate.

After decanting, the chlorinated phase is washed with 200 ml of water and then concentrated under reduced pressure.

In this manner, 124.4 g of methyl (R)-2-hydroxy-2(2-chlorophenyl)acetate is obtained in the form of a colourless oil.

Yield: 94% Optical purity by liquid chromatography of the chiral phase: >99% NMR (CDCl$_3$): 7.4–7.2 ppm (multiplet 4 aromatic protons) 5.57 ppm (singlet, 1 CH proton) 3.76 ppm (singlet, 3 OCH$_3$ protons) 3.59 ppm (wide singlet, 1 OH proton)

EXAMPLES 1 TO 7

Methyl (R)-2-benzenesulphonyloxy-2(2-chlorophenyl)acetate

EXAMPLE 1

In a dry, 100-ml tricol round-bottomed flask, fitted with a magnetic stirrer, a condenser and a thermometer and operating under an atmosphere of nitrogen, is taken 3.81 g (36 mmoles) of lithium perchlorate, 30 mmoles of benzenesulphonyl chloride and 45 ml of dichloroethane.

To the solution obtained, is added 2.9 ml (36 mmoles) of pyridine. The non-uniform white reaction medium is then stirred for 15 minutes before adding 6.0 g of methyl (R)-2-hydroxy-2(2-chlorophenyl)acetate dissolved in 15 ml of dichloroethane.

The milky reaction mixture obtained is stirred for 5 hours and then poured over a stirred mixture of 120 ml of 1N hydrochloric acid and 240 ml of dichloromethane. After decanting, the chlorinated phase is washed with 120 ml of water and then concentrated under reduced pressure. The sulphonate thus formed takes the form of a colourless, viscous liquid. Purification on a silica column yields an analytically pure sample. In this manner, methyl (R)-2-benzenesulphonyloxy-2(2-chlorophenyl)acetate is obtained.

Yield: 90% Optical purity: >99% $[\alpha]_{589}^{25}$: −53° (2%, methanol) NMR (CDCl$_3$) 7.88 ppm (doublet of triplets, 2 aromatic protons) 7.63 to 7.55 ppm (multiplet, 1 aromatic proton) 7.50 to 7.38 ppm (multiplet, 3 aromatic protons) 7.33 to 7.17 ppm (multiplet, 3 aromatic protons) 6.30 ppm (singlet, 1 (CH) proton) 3.70 ppm (singlet, 1 (OCH$_3$) proton).

Following the same process as that described previously, the following compounds have been prepared:

(R)-2(2-chlorophenyl)-2(4-p-toluenesulphonyloxy) acetate

EXAMPLE 2

Yield: 85% Optical purity: >99% $[\alpha]_{589}^{25}$ −58.3° (2%, methanol) NMR (CDCl$_3$) 7.75 to 7.25 ppm (multiplets, 8 aromatic protons) 5.79 ppm (singlet, 1 (CH—O) proton) 3.67 ppm (singlet, 3 (OCH$_3$) protons) 2.41 ppm (singlet, 3 (CH$_3$-phenyl) protons)

Methyl
(R)-2(2-chlorophenyl)-2-methanesulphonyloxy
acetate

EXAMPLE 3

Yield: 87% Optical purity: >99% $[\alpha]_{589}^{25}$ –75.6° (2%, methanol) NMR (CDCl$_3$) 7.49 to 7.28 ppm (multiplets, 4 aromatic protons) 6.40 ppm (singlet, 1 (CH) proton) 3.79 ppm (singlet, 3 (OCH$_3$) protons) 3.14 ppm (singlet, 3 (SO$_2$CH$_3$) protons)

Methyl (R)-2(4-chlorobenzenesulphonyloxy)-2(2-chlorophenyl)acetate

EXAMPLE 4

Yield: 90% Optical purity: >99% NMR (CDCl$_3$) 7.8 and 7.43 ppm (2 doublets, 4 aromatic protons) 7.42 to 7.18 ppm (multiplet, 4 aromatic protons) 6.31 ppm (singlet, 1 (CH) proton) 3.73 ppm (singlet, 3 (OCH$_3$) protons)

Methyl (R)-2(2-chlorophenyl)-2(2,4,6-trimethylbenzenesulphonyloxy)acetate

EXAMPLE 5

Yield: 93% Optical purity: >99% NMR (CDCl$_3$) 7.50 to 7.20 ppm (multiplet, 4 aromatic protons) 6.92 ppm (singlet, 2 aromatic protons) 6.21 ppm (singlet, 1 (CH) proton) 3.69 ppm (singlet, 3 (OCH$_3$) protons) 2.62 ppm (singlet, 6 (CH$_3$) protons) 2.30 ppm (singlet, 3 (CH$_3$) protons)

Methyl (R)-2(2-chlorophenyl)-2(2,4,6-triisopropyl-benzenesulphonyloxy)acetate

EXAMPLE 6

Yield: 93% Optical purity: >99% NMR (CDCl$_3$) 7.50 to 7.20 ppm (multiplet, 4 aromatic protons) 7.14 ppm (singlet, 2 aromatic protons) 6.25 ppm (singlet, 1 (CH) proton) 4.09 ppm (septuplet, 2 (2CH-isopropyl) protons) 3.71 ppm (singlet, 3 (OCH$_3$) protons) 2.85 ppm (septuplet, 1 (CH isopropyl) proton) 1.24 ppm (doublet, 6 (2 CH$_3$) protons) 1.22 ppm (doublet, 6 (2 CH$_3$) protons) 1.10 ppm (doublet, 6 (2 CH$_3$) protons)

Methyl (R)-2(2-chlorophenyl)-2(4-nitrobenzene-sulphonyloxy)acetate

EXAMPLE 7

Yield: 92% Optical purity: >99% NMR (CDCl$_3$) 8.29 and 8.06 ppm (2 doublets, 4 aromatic protons) 7.40 to 7.15 ppm (multiplet, 4 aromatic protons) 6.37 ppm (singlet, 1 (CH) proton) 3.74 ppm (singlet, 3 (OCH$_3$) protons)

EXAMPLE 8

Methyl
(R)-2-benzenesulphonyloxy-2(2-chlorophenyl)acetate

In a dry, tricol round-bottomed flask, fitted with a double-jacket, a magnetic stirrer, a condenser and a thermometer and operating under an atmosphere of nitrogen, is taken 0.72 g (6 mmoles) of 4-dimethylaminopyridine, 12.0 g (60 mmoles) of methyl (R)-2-hydroxy-2(2-chlorophenyl)acetate, 6.06 g (60 mmoles) of triethylamine and then 20 ml of dichloromethane. The colourless solution obtained is cooled to 0° C. and then, operating at this temperature, 60 mmoles of benzenesulphonyl chloride in solution in 30 ml of dichloromethane is added. The reaction mixture is stirred for 3 hours at 0° C. and then tipped onto a stirred mixture consisting of 240 ml of 1N hydrochloric acid and 240 ml of dichloromethane.

After decanting, the chlorinated phase is washed with 120 ml of water and then concentrated under reduced pressure.

The sulphonate thus formed takes the form of a colourless viscous liquid. An analytically pure sample is obtained after purifying on a silica column.

In this manner; methyl (R)-2-benzenesulphonyloxy-2(2-chlorophenyl)acetate is obtained:

Yield: 97% Optical purity: >99% $[\alpha]_{589}^{25}$ –53° (2%, methanol)

Following the same process as that described above, the following compounds are obtained:

Methyl (R)-2(2-chlorophenyl)-2(4-nitrobenzene-sulphonyloxy)acetate

EXAMPLE 9

Yield: 88% Optical purity: >99%

Methyl (R)-2(2-chlorophenyl)-2(2,5-dichlorobenzenesulphonyloxy)acetate

EXAMPLE 10

Yield: 95% Optical purity: >99% NMR (CDCl$_3$) 7.98 ppm (doublet, 1 aromatic proton) 7.15 to 7.50 ppm (multiplets, 6 aromatic protons) 6.38 ppm (singlet, 1 (CH) proton) 3.74 ppm (singlet, 3 (OCH$_3$) protons)

EXAMPLE 11

Methyl
(R)-2-benzenesulphonyloxy-2(2-chlorophenyl)acetate

This compound was obtained using the method described in Example 8, but replacing the dichloromethane by toluene.
Yield: 95%

EXAMPLE 12

Methyl
(R)-2-benzenesulphonyloxy-2(2-chlorophenyl)acetate

In a dry, tricol round-bottomed flask, fitted as in Example 8 is taken 0.72 g (6 mmoles; 0.1 equivalent) of 4-dimethylaminopyridine, 12.0 g (60 mmoles; 1 equivalent) of methyl (R)-2-hydroxy-2(2-chlorophenyl)acetate and 7.8 g (78 mmoles; 1.3 equivalent) of triethylamine and 20 ml of dichloromethane. The colourless solution obtained is cooled to 0° C. and then, operating at this temperature, 6.06 g (60 mmoles; 1 equivalent) of benzenesulphonyl chloride in solution in 30 ml of dichloromethane. The reaction mixture is stirred for 3 hours at 0° C. and then tipped onto a stirred mixture consisting of 240 ml of 1N hydrochloric acid and 240 ml of dichloromethane, while stirring this mixture.

After decanting, the chlorinated phase is washed with dilute hydrochloric acid and then with water, before being concentrated under reduced pressure. An analytically pure sample is obtained after purifying on a silica column.

In this manner, methyl (R)-2-benzenesulphonyloxy-2-(2-chlorophenyl)acetate is obtained:

Yield: 98% Optical purity: 100% (S(+) enantiomer not detected)

EXAMPLE 13

Methyl (S)-2(2-chlorophenyl)-2(4,5,6,7-tetrahydrothieno[3,2-c]-5-pyridyl)acetate In a dry, 50-ml tricol round-bottomed flask, fitted with a double jacket, a magnetic stirrer, a condenser and a thermometer, is taken Y mmoles of 4,5,6,7-tetrahydrothieno[3,2-c]pyridine in solution in 7.5 ml of solvent and 2.85 g of a 30% aqueous solution of potassium carbonate. After stirring for 10 minutes, 5 mmoles of the formula-I compound, previously dissolved in 2.5 ml of solvent, is added.

The two-phase medium thus obtained is heated under reflux for the time indicated and then cooled to 70° C. and decanted.

In this manner, methyl (S)-2(2-chlorophenyl)-2(4,5,6,7-tetrahydrothieno[3,2-c]-5-pyridyl)acetate or clopidogrel is obtained NMR (CDCl$_3$) 7.70 ppm (multiplet, 1 aromatic proton of benzene) 7.41 ppm (multiplet, 1 aromatic proton of benzene) 7.33 to 7.22 ppm (multiplet, 2 aromatic protons of benzene) 7.06 ppm (doublet, 1 aromatic proton of thiophene) 6.67 ppm (doublet, 1 aromatic proton of thiophene) 4.93 ppm (singlet, 1 CHCO proton) 3.73 ppm (singlet, 3 OCH$_3$ protons) 3.76 and 3.64 ppm (2 doublets, 2 CH$_3$ protons) 2.89 ppm (singlet, 4 2CH$_2$ protons)

Depending on the formula-I compounds used, the concentrations of 4,5,6,7-tetrahydrothieno[3,2-c]pyridine used, the yields obtained using the above solvents and reaction times are as follows:

EXAMPLE 14

Methyl (S)-2(2-chlorophenyl)-2(4,5,6,7-tetrahydrothieno[3,2-c]-5-pyridyl)acetate In a 50-ml tricol round-bottomed flask, fitted with a double-jacket, a magnetic stirrer, a condenser and a thermometer is taken 1.2 mmoles of 4,5,6,7-tetrahydrothieno[3,2-c]pyridine in solution in 7.5 ml of dichloromethane and 2.85 g of a 30% aqueous solution of potassium carbonate. After stirring for 10 minutes, 5 mmoles of methyl (R)-2(2-chlorophenyl)-2(2,5-dichlorobenzenesulphonyloxy)acetate, previously dissolved in 2.5 ml of solvent is added.

The two-phase medium thus obtained is heated under reflux for 3.5 hours, cooled to 70° C. and then decanted.

In this manner, methyl (S)-2(2-chlorophenyl)-2(4,5,6,7-tetrahydrothieno[3,2-c]-5-pyridyl)acetate is obtained.

Yield: 89% Optical purity: 96%

EXAMPLE 15

Methyl (S)-2(2-chlorophenyl)-2(4,5,6,7-tetrahydrothieno[3,2-c]-5-pyridyl)hemisulphate or clopidogrel hemisulphate a) Methyl (+)-(S)-α-(2-thien-2-yl)ethylamino)-α-(2-chlorophenyl)acetate In a 250-ml reactor, fitted with a double jacket, a motor-driven stirrer, a condenser and a thermometer is taken 7.62 g of 2(thien-2-yl)ethylamine (0.06 mole; 1.2 molar equivalent in terms of the sulphonyloxy derivative) in solution in 67.5 ml of dichloromethane and an aqueous solution of 7.0 g of potassium bicarbonate (0.07 mole; 1.4 equivalent in terms of the sulphonyloxy derivative) in 30 ml of water. After stirring for 5 minutes, 0.05 mole (1 equivalent) of the formula-I compound is added, dissolved in 40 ml dichloromethane.

The two-phase medium thus obtained is heated under reflux for the time indicated, cooled and then decanted and the (+) methyl (S)-α(2-thien-2-yl)ethylamino-α(2-chlorophenyl)acetate (formula IV) is collected.

Depending on the formula-I compounds used and with the above reaction times, the following yields are obtained:

| Formula-I compound | Y | | Reaction time | Clopidogrel | |
| --- | --- | --- | --- | --- | --- |
| R1 | (mmoles) | Solvent | (h) | Yield (%) | Optical purity (%) |
| Phenyl | 5 (1.7 g; 1 equivalent) | toluene | 4.5 | 85 | 90 |
| Phenyl | 6 (1.2 equivalent) | dichloromethane | 5 | 94.5 | 96.2 |
| Phenyl | 12.5 (2.5 equivalent) | dichloromethane | 5 | 98.5 | 89 |
| 4-chlorophenyl | 6 | dichloromethane | 10 | about 100 | 96 |
| 4-nitrophenyl | 6 | dichloromethane | 0.5 | about 100 | >98 |

| Formula-I compound | Formula IV-compound | | |
|---|---|---|---|
| R1 | Reaction time (h) | Yield (%) | Optical purity (%) |
| methyl | 29 | 65 | 76 |
| phenyl | 22 | 71 | 92 |
| 4-chlorophenyl | 11 | 94 | 92 |
| 4-nitrophenyl | 2 | 99 | 95 |
| 2,5-dichlorophenyl | 6 | 98 | 97 | b) Clopidogrel Hemisulphate

While stirring, 20.5 g of (+) methyl (S)-α(2-thien-2-yl)ethylamino-α(2-chlorophenyl)acetate in solution in 200 ml of methylene chloride is added over 25 minutes to 40 ml of 30% (w/w) of an aqueous solution of formic aldehyde.

After stirring for 3 hours, the organic phase is decanted, washed with water, dried and the solvent evaporated. The residue is dissolved in 50 ml of methylene chloride and the solution, at a temperature of 60° C., is added to 100 ml of anhydrous N,N-dimethylformamide containing 6N hydrochloric acid. After one hour and a half, the solvents are eliminated by distilling under reduced pressure and the residue is dissolved in 200 ml of methylene chloride and 100 ml water.

Sodium bicarbonate is added to release the base from its hydrochloride, the organic phase decanted, dried and concentrated under reduced pressure, which yields clopidogrel in the form of the free base.

The hemisulphate of this basic, compound is then formed in 150 ml of acetone by reacting with 4.9 g of concentrated sulphuric acid (96%).

In this manner, 17 g of clopidogrel hemisulphate is obtained.

$[\alpha]_D^{20} = 53°$ (C=1, methanol)

The invention claimed is:

1. A process for the preparation of a compound having the formula:

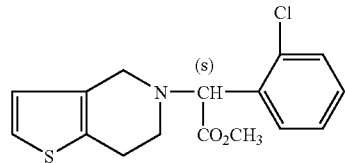

which comprises reacting 2-(thien-2-yl)ethylamine having the formula lp;-1p 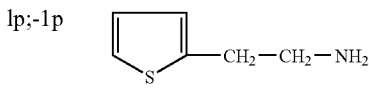

in the form of a base or a salt, with an (R)-sulphonyloxyacetic ester having the formula

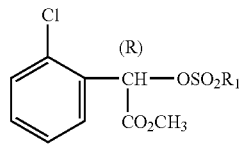

wherein $R_1$ is benzyl, $C_1$–$C_4$-alkyl optionally substituted by one or more halogens, or phenyl optionally substituted by nitro, one or more halogens or one or more $C_1$–$C_4$-alkyl groups, in the presence of a base, used alone or in aqueous solution and reacting the resulting compound of the formula

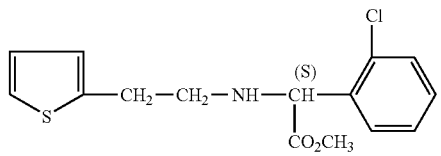

with a formylation agent, and effecting cyclization in the presence of an acid to give the desired compound.

2. A process according to claim 1 wherein the formylation agent is chosen from formaldehyde, its hydrate or its polymerisation derivatives, compounds with the general formula:

in which $R_3$ represents a halogen atom, a $C_1$–$C_4$ alkoxy group, a $C_1$–$C_4$ alkylthio group or an amino group and $R_4$ represents a $C_1$–$C_4$ alkoxy group, a $C_1$–$C_4$ alkylthio group, a $C_2$–$C_5$ alkoxycarbonyl or phenoxycarbonyl group or heterocyclic compounds with the general formula:

in which Z represents O, NH, or S.

3. A process according to claim 2 wherein the formylation agent is chosen from formaldehyde, its hydrate or its polymerisation derivatives.

4. A process according to claim 1 wherein the reaction with the (R)-sulphonyloxyacetic ester takes place in a polar or non-polar solvent.

5. A process according to claim 1 wherein the reaction with the formylation agent and the cyclisation take place simultaneously in a polar solvent.

6. A process according to claim 5 wherein the acid is formic acid, which is also used as the solvent.

7. A process according to claim 1 wherein $R_1$ is phenyl, 4-chlorophenyl, 4-nitrophenyl or 2,5-dichlorophenyl.

8. A process according to claim 1 wherein formylation and cyclization take place successively.

9. A process for the preparation of a compound having the formula

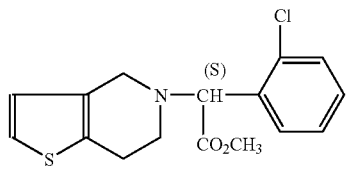

which comprises reacting a compound having the formula

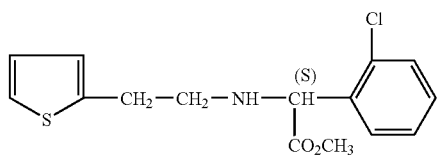

with a formylation agent and cyclizing the resulting product.

10. A process according to claim 9 wherein the formylation agent is formaldehyde.

11. A process according to claim 10 wherein cyclization takes place in the presence of hydrochloric acid.

* * * * *